US00PP20708P2

(12) United States Plant Patent
Miedema-Jorna

(10) Patent No.: US PP20,708 P2
(45) Date of Patent: Feb. 2, 2010

(54) **NEW GUINEA *IMPATIENS* PLANT NAMED 'FIDIMPPI'**

(50) Latin Name: *Impatiens hawkeri*
Varietal Denomination: Fidimppi

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/291,391

(22) Filed: Nov. 7, 2008

(51) Int. Cl.
*A01H 5/00* (2006.01)

(52) U.S. Cl. ..... Plt./318.5

(58) Field of Classification Search ..... Plt./318.5
See application file for complete search history.

*Primary Examiner*—Kent L Bell
(74) *Attorney, Agent, or Firm*—C. A. Whealy

(57) ABSTRACT

A new and distinct cultivar of *Impatiens* plant named 'Fidimppi', characterized by its upright and outwardly spreading growth habit; mounded plant form; freely branching habit; dark green-colored leaves; freely flowering habit; large intense dark pink-colored flowers; and good garden performance.

1 Drawing Sheet

Botanical designation: *Impatiens hawkeri.*
Cultivar denomination: 'Fidimppi'.

BACKGROUND OF THE INVENTION

The present invention relates to a new and distinct cultivar of New Guinea *Impatiens* plant, botanically known as *Impatiens hawkeri* and hereinafter referred to by the name 'Fidimppi'.

The new *Impatiens* plant is a product of a planned breeding program conducted by the Inventor in De Lier, The Netherlands. The objective of the breeding program is to create new freely-branching New Guinea *Impatiens* plants with freely flowering habit and large attractive flowers.

The new *Impatiens* plant originated from a cross-pollination made by the Inventor in De Lier, The Netherlands of a proprietary selection of *Impatiens hawkeri* identified as code number AMI 081120, not patented, as the female, or seed, parent with a proprietary selection of *Impatiens hawkeri* identified as code number AMI 081130, not patented, as the male, or pollen, parent. The new *Impatiens* was discovered and selected by the Inventor as a single flowering plant within the progeny of the stated cross-pollination in a controlled environment in De Lier, The Netherlands in 2005.

Asexual reproduction of the new *Impatiens* by vegetative cuttings in a controlled environment in De Lier, The Netherlands since 2006, has shown that the unique features of this new *Impatiens* are stable and reproduced true to type in successive generations.

SUMMARY OF THE INVENTION

Plants of the new *Impatiens* plant have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fidimppi'. These characteristics in combination distinguish 'Fidimppi' as a new and distinct cultivar of *Impatiens:*

1. Upright and outwardly spreading growth habit; mounded plant form.

2. Freely branching habit.
3. Dark green-colored leaves.
4. Freely flowering habit.
5. Large intense dark pink-colored flowers.
6. Good garden performance.

Plants of the new *Impatiens* can be compared to plants of the female parent selection. Plants of the new *Impatiens* differ from plants of the female parent selection in the following characteristics:

1. Plants of the new *Impatiens* flower later than plants of the female parent selection.
2. Flowers of plants of the new *Impatiens* do not fade with development whereas flowers of plants of the female parent selection fade with development.

Plants of the new *Impatiens* can be compared to plants of the male parent selection. Plants of the new *Impatiens* differ from plants of the male parent selection in the following characteristics:

1. Plants of the new *Impatiens* are more vigorous than plants of the male parent selection.
2. Plants of the new *Impatiens* have smaller flowers than plants of the male parent selection.

Plants of the new *Impatiens* can be compared to plants of *Impatiens* 'Fitam Light Pink', disclosed in U.S. Plant Pat. No. 15,223. In side-by-side comparisons conducted in De Lier, The Netherlands, plants of the new *Impatiens* differed from plants of 'Fitam Light Pink' in the following characteristics:

1. Plants of the new *Impatiens* were more vigorous than plants of 'Fitam Light Pink'.
2. Flowers of plants of the new *Impatiens* were darker pink in color than plants of 'Fitam Light Pink'.

BRIEF DESCRIPTION OF THE PHOTOGRAPH

The accompanying colored photograph illustrates the overall appearance of the new *Impatiens,* showing the colors as true as it is reasonably possible to obtain in colored reproductions of this type. Colors in the photograph may differ slightly from the color values cited in the detailed botanical description which accurately describe the colors of the new *Impatiens* plant.

The photograph comprises a top perspective view of a typical flowering plant of 'Fidimppi' grown in a container.

DETAILED BOTANICAL DESCRIPTION

The aforementioned photographs and following observations, measurements and values describe plants grown in De Lier, The Netherlands, in 12-cm containers and under commercial practice during the summer in a glass-covered greenhouse with day and night temperatures averaging 18° C. Plants had been growing for nine weeks when the photograph and description were taken. In the following description, color references are made to The Royal Horticultural Society Colour Chart, 2001 Edition, except where general terms of ordinary dictionary significance are used.

Botanical classification: *Impatiens hawkeri* 'Fidimppi'.

Parentage:

*Female, or seed, parent*.—Proprietary selection of *Impatiens hawkeri* identified as code number AMI 081120, not patented.

*Male, or pollen, parent*.—Proprietary selection of *Impatiens hawkeri* identified as code number AMI 081130, not patented.

Propagation:

*Type*.—By vegetative cuttings.

*Time to initiate roots, summer*.—About five to seven days at temperatures of 19° C. to 20° C.

*Time to initiate roots, winter*.—About six to eight days at temperatures of 19° C. to 20° C.

*Time to produce a rooted young plant, summer*.—About 14 to 19 days at temperatures of 19° C. to 20° C.

*Time to produce a rooted young plant, winter*.—About 14 to 21 days at temperatures of 19° C. to 20° C.

*Root description*.—Fine; white to brown in color.

*Rooting habit*.—Freely branching.

Plant description:

*Plant and growth habit*.—Upright and outwardly spreading growth habit; mounded plant form. Freely branching habit with about eight lateral branches; pinching is typically not required. Moderately vigorous growth habit.

*Plant height*.—About 22 cm.

*Plant diameter*.—About 34 cm.

Lateral branch description:

*Length*.—About 18 cm.

*Diameter*.—About 9 mm.

*Internode length*.—About 3.5 cm.

*Strength*.—Moderately strong.

*Aspect*.—Initially upright to outwardly spreading.

*Texture*.—Smooth, glabrous.

*Color*.—Close to 173A; at the nodes, tinted with close to 181A.

Foliage description:

*Arrangement*.—Opposite or in whorls of about five; simple.

*Length*.—About 12.5 cm.

*Width*.—About 4.5 cm.

*Shape*.—Elliptic.

*Apex*.—Acute.

*Base*.—Attenuate.

*Margin*.—Serrate with ciliation.

*Texture, upper and lower surfaces*.—Smooth, glabrous; leathery; moderately glossy in luster.

*Venation pattern*.—Pinnate; arcuate.

*Color*.—Developing leaves, upper surface: Close to N137A. Developing leaves, lower surface: Close to 138B. Fully expanded leaves, upper surface: Between 136A and 139A; venation, close to 183B. Fully expanded leaves, lower surface: Close to 138B; venation, close to 183A.

*Petiole*.—Length: About 2 cm. Diameter: About 3 mm. Texture, upper and lower surfaces: Smooth, glabrous. Color, upper and lower surfaces: Close to 181A to 181C.

Flower description:

*Flower type and flowering habit*.—Single rounded axillary flowers. Freely flowering habit with numerous flowers developing continuously per lateral branch. Flowers positioned above the foliage and typically face upright or outward. Flowers last about ten days on the plant under greenhouse conditions. Petals self-cleaning, gynoecium persistent. Flowers not fragrant.

*Natural flowering season*.—Year-round under greenhouse conditions. In the garden, flowering from spring through summer in The Netherlands. Plants begin flowering about nine weeks after planting.

*Flower size*.—Diameter: About 7.4 cm. Depth: About 1 cm.

*Flower buds*.—Length: About 2.1 cm. Diameter: About 1.4 cm. Shape: Ovoid; pointed. Color: Between N57C and 58A.

*Petals*.—Quantity/arrangement: Five per flower in a single whorl. Length, banner petal: About 2.6 cm. Length, lateral and lower petals: About 3.2 cm. Width, banner petal: About 5.1 cm. Width, lateral and lower petals: About 3.8 cm. Shape, all petals: Broadly cordate. Apex, all petals: Deeply emarginate. Base, all petals: Attenuate. Margin, all petals: Entire. Texture, all petals, upper and lower surfaces: Smooth, glabrous. Color, banner petal: When opening and fully opened, upper surface: Between 58B to 58C; towards the base, close to 63A; color does not fade with development. When opening and fully opened, lower surface: Close to 58C; central zone, close to 63A; central stripe, close to 59A to 59B. Color, lateral and lower petals: When opening and fully opened, upper surface: Close to 58B to 58C; towards the base, close to 63A; color does not fade with development. When opening and fully opened, lower surface: Close to 58C; central zone, close to 63B; central stripe, close to 63B.

*Sepals*.—Quantity/arrangement: Three; one modified into an elongated spur. Length, spurred sepal: About 1.4 cm. Length, lateral sepals: About 1.4 cm. Width, spurred sepal: About 1.2 cm. Width, lateral sepals: About 6 mm. Shape, spurred sepal: Broadly ovate with elongate spur. Shape, lateral sepals: Ovate. Apex, all sepals: Apiculate. Base, all sepals: Cuneate. Margin, all sepals: Entire. Texture, all sepals, upper and lower surfaces: Smooth, glabrous. Color, spurred sepal: Upper surface: Towards the base, close to 63A to 63B; towards the apex, close to 144C. Lower surface: Towards the base, close to 63A; towards the apex, close to 144C. Color, lateral sepals: Upper surface: Towards the base, close to 63A to 63B; towards the apex, close to 144C. Lower surface: Towards the base, close to 63A; towards the apex, close to 144C. Spur length: About 5.5 cm. Spur diameter: At flower, about 2 mm; at apex, less than 1 mm. Spur texture:

Smooth, glabrous. Spur color: Close to 60A; with development, becoming closer to 185A.

*Peduncles*.—Length: About 5.5 cm. Diameter: About 2 mm. Angle: Mostly erect. Strength: Moderately strong. Texture: Smooth, glabrous. Color: Between 59A and 60A.

*Reproductive organs*.—Stamens: Quantity: Five fused at anthers; filaments free. Anther length: About 3 mm. Anther color: Close to 61B to 61D. Pollen amount: Scarce. Pollen color: Close to 158D. Pistils: Quantity per flower: One. Pistil length: About 0.5 mm. Stigma shape: Capitate. Stigma color: Close to 158D. Ovary color: Close to N144A tinted with close to 183B.

*Seed/fruit*.—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate wind, rain and temperatures ranging from about 4° C. to about 35° C.

It is claimed:

1. A new and distinct *Impatiens* plant named 'Fidimppi' as illustrated and described.

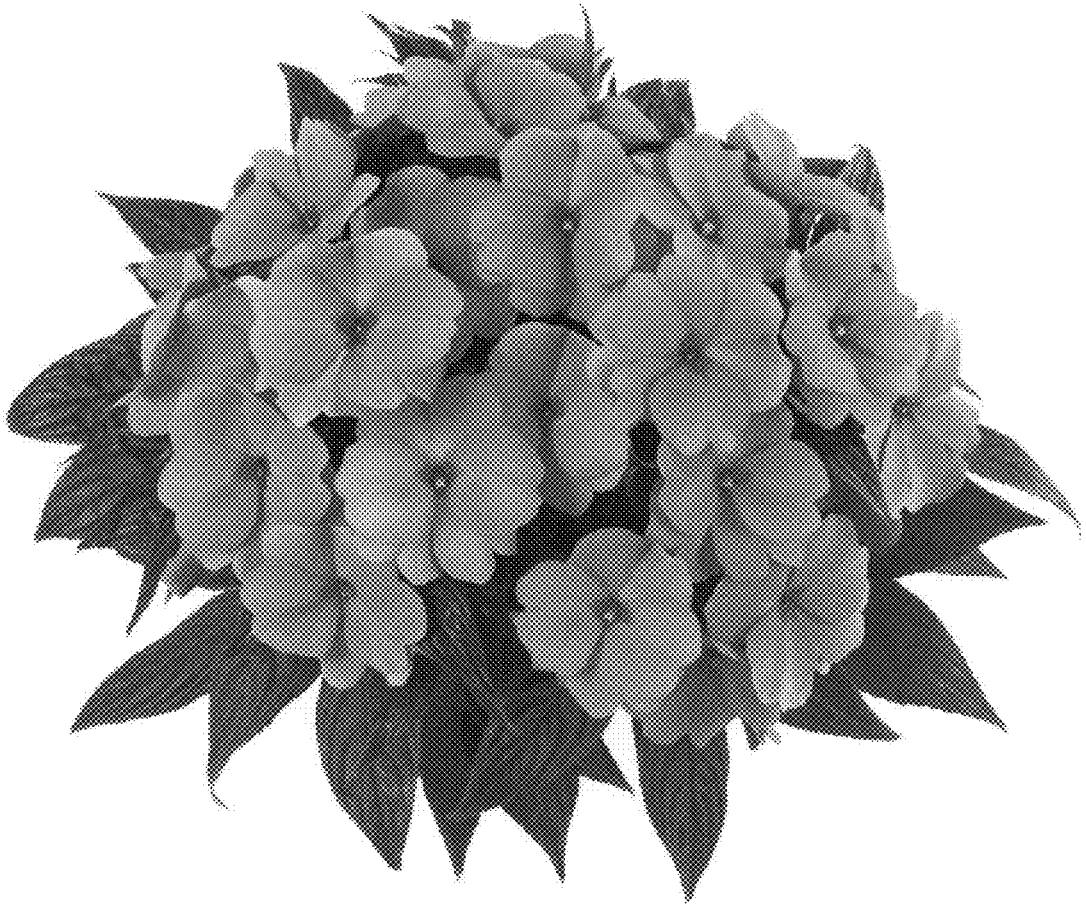

* * * * *